US005573956A

United States Patent [19]

Hanning

[11] Patent Number: 5,573,956
[45] Date of Patent: Nov. 12, 1996

[54] ASSAY METHOD BASED UPON REFRACTIVE INDEX CHANGES AT A SOLID OPTICAL SURFACE

[76] Inventor: Anders Hanning, Fjällvägen 6B, S-191 46 Sollentuna, Sweden

[21] Appl. No.: 193,128

[22] PCT Filed: Aug. 19, 1992

[86] PCT No.: PCT/SE92/00558

§ 371 Date: Feb. 18, 1994

§ 102(e) Date: Feb. 18, 1994

[87] PCT Pub. No.: WO93/04357

PCT Pub. Date: Mar. 4, 1993

[30] Foreign Application Priority Data

Aug. 20, 1991 [SE] Sweden .................................. 9102397
Mar. 25, 1992 [SE] Sweden .................................. 9200917

[51] Int. Cl.$^6$ .................................................. G01N 33/543
[52] U.S. Cl. .................... 436/518; 356/318; 356/445; 385/12; 385/129; 385/130; 422/82.05; 422/82.08; 422/82.11; 435/808; 436/164; 436/165; 436/524; 436/525; 436/527; 436/805
[58] Field of Search ................................ 356/317, 318, 356/445; 385/12, 129, 130; 422/82.05, 82.08, 82.11; 435/7.9, 7.92, 7.93, 7.94, 808; 436/164, 165, 518, 524, 525, 527, 805

[56] References Cited

U.S. PATENT DOCUMENTS

| | | | |
|---|---|---|---|
| 4,844,613 | 7/1989 | Batchelder et al. | 356/445 |
| 4,889,427 | 12/1989 | Van Veen et al. | 356/445 |
| 4,954,435 | 9/1990 | Krauth | 436/531 |
| 4,978,503 | 12/1990 | Shanks et al. | 422/82.11 |
| 4,997,278 | 3/1991 | Finlan et al. | 356/445 |

FOREIGN PATENT DOCUMENTS

| | | |
|---|---|---|
| 0276142 | 7/1988 | European Pat. Off. . |
| 0341927 | 11/1989 | European Pat. Off. . |
| 0341928 | 11/1989 | European Pat. Off. . |

OTHER PUBLICATIONS

Applied Optics, vol. 30, No. 12, 20 Apr. 1991, p. 1474–1479 R. G. Heideman et al: "Simple interferometer for evanescent field refractive index sensing as a feasibility study for an immunosensor".

Van Gent et al. (1989) *Sensors and Actuators* 17: 297–305.

Van Gent et al. (1991) *Sensors and Actuators* 25–27: 449–452.

Pockrand et al. (1978) *J. Optical Society of America* 68:1147–1151.

Pockrand et al. (1978) *J. Chem. Phys.* 69(9): 4001–4011.

Wahling et al. (1978) *Z. Naturforsch.* 33a:907–909.

G. Wahling (1981) *Z. Naturforsch.* 36a:588–594.

Gauglitz et al. (1988) *Anal. Chem.* 60: 2609–2612.

Biosensors & Bioelectronics, 215–225, 6 (1991) (Great Britain) W. Lukosz: "Principles and sensitivities of integrated optical and surface plasmon sensors for direct affinity sensing and immunosensing".

International Publication WO 90/05295 published May 17, 1990.

International Publication WO 90/11525 published Oct. 4, 1990.

Biosensors & Bioelectronics, 201–214, 6 (1991) (Great Britain) J. W. Attridge et al: "Sensitivity enhancement of optical immunosensors by the use of a surface plasmon resonance fluoro–immunoassay".

J. van Gent et al., J. Chem. Soc. Chem. Commun. (1988) 893–895.

*Primary Examiner*—James C. Housel
*Assistant Examiner*—Christopher L. Chin
*Attorney, Agent, or Firm*—Birch, Stewart, Kolasch and Birch, LLP

[57] ABSTRACT

A method of assaying for an analyte in a fluid sample comprises detecting the presence of the analyte by determining the resulting change in refractive index at a solid optical surface in contact with the sample, which change is caused by the analyte involving or influencing the binding or release of a refractive index-enhancing species to or from, respectively, the optical surface. Determination is performed with light having a wavelength at or near the maximum of the negative derivative of the absorptivity with respect to wavelength of the refractive index-enhancing species to obtain maximum sensitivity.

14 Claims, 1 Drawing Sheet

ASSAY METHOD BASED UPON REFRACTIVE INDEX CHANGES AT A SOLID OPTICAL SURFACE

BACKGROUND OF THE INVENTION

1. Field of the Invention

The present invention relates to an improvement in assays of the type wherein the presence of the analyte is detected by determining a change in refractive index at a solid optical surface, which change is caused by the analyte involving or influencing the binding of a refractive index enhancing species to the optical surface, or the release therefrom, respectively.

One type of method for determining such refractive index changes at an optical surface is based upon surface plasmon resonance, hereinafter SPR. The phenomenon of SPR is well known. In brief, SPR is observed as a dip in intensity of light reflected at a specific angle from the interface between an optically transparent material, e.g. glass, and a thin metal film, usually silver or gold, and depends on among other factors the refractive index of the medium (e.g., a sample solution) close to the metal surface. A change of refractive index at the metal surface, such as by the adsorption or binding of material thereto, will cause a corresponding shift in the angle at which SPR occurs. To couple the light to the interface such that SPR arises, two alternative arrangements are used, either a metallized diffraction grating (Wood's effect), or a metallized glass prism or a prism in optical contact with a metallized glass substrate (Kretschmann effect). For further details on SPR, reference is made to our WO 90/05295. In an SPR-based immunoassay, a ligand may be bound to the metal surface, and the interaction thereof with an analyte of an aqueous sample in contact with the surface is monitored.

Water and diluted aqueous buffers have a refractive index of about 1.33, whereas most proteins have a refractive index in the region of about 1.5 to 1.6. Since the SPR-measurement response is proportional to the change in refractive index caused when, e.g., protein molecules are adsorbed to the surface and displace water therefrom, the refractive index difference between the protein and the buffer solution puts a theoretical limit to the strength of response that may be obtained.

It is understood that SPR-based immunoassays for substances of low molecular weight or occurring in low concentrations, like, for instance, haptens, are problematic due to the very small changes in refractive index caused when the analyte binds to or dissociates from the antibody-coated sensing surface.

2. Description of Related Art

Attempts to obviate this problem in SPR-immunoassays are described in EP-A-276 142 and WO 90/11525 (the former specifically making use of the above mentioned Wood's effect, and the latter of the Kretschmann effect).

Both publications disclose the conjugation of a reagent (for example the analyte or an analyte analogue in a competition assay) with a refractive index increasing species or probe. Such a probe may, for instance, be a molecule or particle having a high refractive index and/or a large size. Possible substances include heavy substances (such as metal ions or higher halogens), highly electronically delocalized species (such as polycyclic aromates or dyes), metal or metal oxide particles (such as titania particles), or high refractive index organic species (such as ferritin). The substance may, alternatively, be one of a lower refractive index than that of the environment close to the sensing surface. The substance may also be an enzyme causing the production of a reaction product which is deposited on the sensing surface and which has a refractive index higher or lower than the material present in the thin layer at the sensing surface.

However, among organic species it is difficult to find molecules having a refractive index higher than about 1.6–1.7. Inorganic species, on the other hand, may have refractive indices of about 2–3, but instead they may be difficult to combine chemically with proteins. The possibilities of significantly enhancing the SPR-signals as proposed by the two cited publications are therefore rather limited, unless, of course, extremely large and thereby impractical probes are used. The problem of insufficient sensitivity for certain kinds of analytes in the mentioned types of assays therefore still remains.

SUMMARY OF THE INVENTION

Accordingly, the present invention aims at overcoming the above mentioned problems and increasing the sensitivity substantially in SPR-assays as well as in any other assay based upon the measurement of refractive index changes at a sensing surface.

In accordance with the present invention, this is achieved by utilizing the fact that the refractive index is highly dependent on the wavelength. This has not been realized or suggested in the above two discussed prior art references where the refractive index in contrast is treated as an indifferent material constant.

Thus, for most substances the refractive index decreases very slowly with increasing wavelength within the visible and near infrared region (normal dispersion). However, in the vicinity of resonance wavelengths, i.e., at light absorption peaks, the refractive index varies heavily, a phenomenon called anomalous dispersion. In this region the refractive index is roughly a function of the negative derivative of the absorptivity (extinction coefficient) with respect to the wavelength. Thus, at a slightly higher wavelength than the resonance wavelength, the refractive index reaches a maximum, i.e., where the negative derivative of the absorptivity has its maximum.

In accordance with the present invention, a considerable increase of the assay sensitivity is therefore obtained if the measurement wavelength is matched with the absorptivity maximum of the refractive index enhancing species used in the particular assays, and more specifically such that the measurement wavelength corresponds to the maximum of the negative derivative of the absorptivity with respect to the wavelength. This may be accomplished either such that the index enhancing species is selected to conform with the measuring wavelength of a particular instrument or application, or that the measuring wavelength is selected to conform with a specific refractive index enhancing species.

It may in this context be mentioned that the use of measurement at or near the absorptivity maximum of chromogenic crown ethers in optochemical sensors based upon SPR has been proposed by J. van Gent et al., Sensors and Actuators, 17 (1989) 297–305. In this prior art case, however, the chromogenic crown ether molecule (a conjugate between a crown ether and a chromophore) is intended to be used as a sensing molecule for calcium and barium ions by detecting the large colour change occurring upon complexation with the metal ions, i.e.., a concept completely different from that of the present invention as will also be clear from the following.

The present invention thus provides a method of assaying for an analyte in a fluid sample, wherein the presence of the analyte is detected by determining the resulting change in refractive index at a solid optical surface in contact with the sample caused by the analyte involving or influencing the binding or release of a refractive index enhancing species to or from, respectively, the optical surface, characterized in that said determination is performed with light having a wavelength at or near the maximum of the negative derivative of the absorptivity with respect to wavelength of said refractive index enhancing species.

In accordance with the invention, the measurement should thus be performed at, or as close as possible to the the maximum of the negative derivative of the absorptivity with respect to wavelength. If the measurement wavelength is chosen on the high wavelength side of the maximum of the negative derivative of the absorptivity with respect to wavelength, the distance between the measurement wavelength and said maximum should preferably be less than 100 nm (corresponding to a possible enhancement of at least about 5 times, on a mass basis, depending on the absorptivity), and more preferably less than 50 nm (corresponding to a possible enhancement of at least about 10 times, on a mass basis). If the measurement wavelength is chosen on the low wavelength side of the maximum of the negative derivative of the absorptivity with respect to wavelength, the measurement wavelength must be very close to said maximum, since the refractive index again decreases when the wavelength of the absorptivity maximum is approached.

Further, the absorptivity (extinction coefficient) of the refractive index enhancing species should be as high as possible preferably higher than 20 $lg^{-1}cm^{-1}$, more preferably higher than 50 $lg^{-1}cm^{-1}$, and especially higher than 100 $lg^{-1}cm^{-1}$.

By proper selection of the refractive index enhancing species or probe, a very high refractive index may thus be obtained. Which specific measuring wavelength to choose for a specific index enhancing species or probe, or vice versa, will, of course, depend on, inter alia, the particular probe, and may readily be established by the skilled person once he has had knowledge of the present invention.

For the purposes of the present invention the refractive index enhancing species or probe preferably is or includes a dye or chromophoric molecule. Usually a dye molecule is conjugated to another molecule, such as a protein or polypeptide (e.g., an antibody or fragment thereof). Exemplary dyes are of the azine, thiazine, oxazine, cyanine, merocyanine, styryl, triphenylmethane, chlorophyll and phthalocyanine types.

The optochemical methods for which the present invention may be used are, as mentioned previously, not restricted to SPR methods, but extend to any assay method measuring a change of the refractive index as being indicative of the presence of an analyte. Such methods include both internal and external reflection methods, for example, ellipsometry and evanescent wave spectroscopy, the latter including Brewster angle reflectometry, critical-angle reflectometry, evanescent wave ellipsometry, scattered total internal reflection (STIR), optical waveguide sensors, etc.

The contact between the fluid sample medium and the optical surface may be static or, preferably, dynamic, i.e.,, by providing the sensing surface or surfaces in some kind of flow cell.

Suitable assay formats for making use of the present invention include, but are, of course, not restricted thereto in any way, those described in the aforementioned WO 90/11525 and EP-A-276 142, including competition assays, displacement assays and sandwich type assays. In a competition assay, the probe will compete with the analyte for the binding to the sensing surface, whereas in a displacement assay the probe is bound to the sensing surface and will be displaced by the analyte. In a sandwich assay, the probe is bound to the analyte, either before or after the latter is bound to the sensing surface.

A competition assay for, for instance a hapten, e.g., theophyllin, may thus be performed by conjugating a suitable probe to theophyllin, and measuring, at or near the absorptivity maximum of the probe, the extent to which the sample, when mixed with the probe, influences, i.e., competes with, the binding of the conjugated theophyllin to the sensing surface.

DETAILED DESCRIPTION OF THE INVENTION

Figure 1:
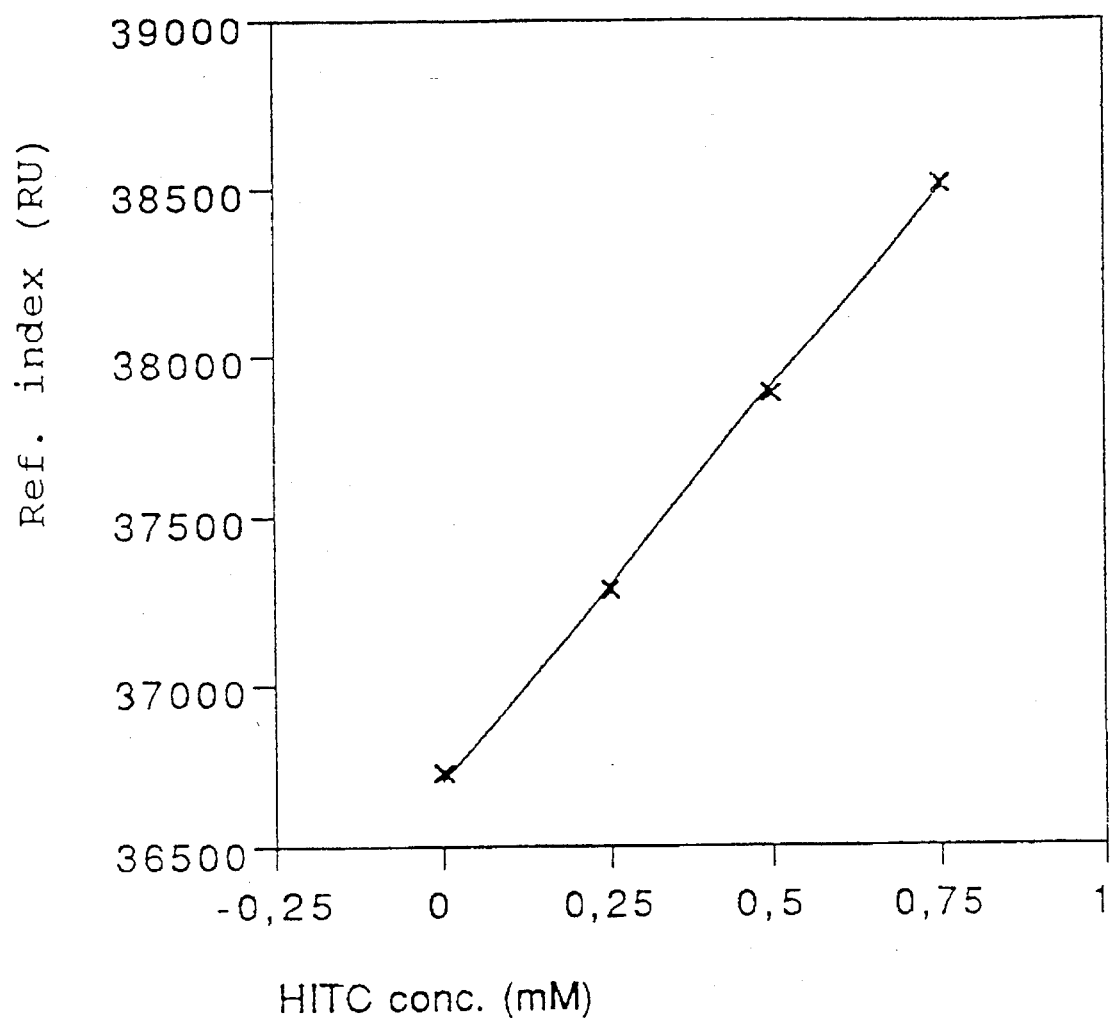
FIG. 1 shows a graph of refractive index vs HITC concentration.

In order to demonstrate the feasibility of the assay method of the present invention, the following experiments were performed with a commercial SPR-based biosensor instrument.

EXAMPLE 1

The dye HITC (1,1',3,3,3',3'-hexamethyl-indotricarbocyanine iodide, 94% purity, Sigma H0387) was dissolved in the concentrations of 0, 0.25, 0.5, and 0.75 mM, respectively, in a mixture of 50% ethanol and 50% citrate buffer (pH 3, 0.1M citrate, 0.5M NaCl, 0.05% Tween® 20) (polyoxyethylene-sorbitan monosaurate. The solutions were injected into a BIAcore™ instrument (marketed by Pharmacia Biosensor AB, Uppsala, Sweden) having a measuring wavelength of 760 nm. Pure citrate buffer was used as eluent, and the refractive index response for each pulse was read. Two test series were run on one and the same sensing surface (Sensor Chip™ CM5, Pharmacia Biosensor AB, Uppsala, Sweden). The repeatability was good.

In FIG. 1 the response (in resonance units, RU) is plotted against HITC concentration. As appears from the graph, the linear fit is good (r>0.999). In combination with the square wave appearance of the pulses, this indicates that only bulk refractive index changes occur and no adsorption of HITC to the sensing surface takes place.

The molar refractive index increment was found to be 2540 RU/mM. With the molecular weight being 537 g/mol, and 1 RU≈$10^{-6}$ refractive index units, the calculated mass-based refractive index increment is 4.73 ml/g (2.540 l·$mol^{-1}$/537 g·$mol^{-1}$). Since proteins in general have a value of 0.185 ml/g, the amplification or enhancement factor in this non-optimized experiment is about 25×. Higher amplification factors would therefore readily seem possible.

An absorption spectrum in the range of 500 to 900 nm was measured with 1 mM HITC diluted to 4 μM with ethanol/citrate. The absorptivity maximum was at 743 nm being 250,000 $cm^{-1}M^{-1}$ or 470 $lg^{-1}cm^{-1}$. The negative absorptivity derivative had its maximum at 760–770 nm and was $-7,500$ $cm^{-}M^{-1}nm^{-1}$ or $-14$ $lg^{-1}cm^{-1}nm^{-1}$. The spectrum obtained was well in conformity with earlier published data.

EXAMPLE 2

Evaluation of the Enhancement By Labeling of a Hapten

The dye 1,1'-di(4-sulfobutyl)-3,3,3',3'-tetramethyl-6-carboxymethyl-indotricarbocyanine, hereinafter referred to as "I" was synthesized according to P. L. Southwick et al., Cytometry, 11 (1990) 418, dye XVIII. This dye is a water-soluble and reactive derivative of the dye HITC used in Example 1 above. The absorption maximum in water was at 746 nm.

0.98 mg (1.2 μmoles) of I activated with TSU (O-(N-succinimidyl)-N,N,N',N'-tetramethyluronium tetrafluoroborate, Fluka) was dissolved in 120 μl of borate buffer (pH 8.5, 0.1 M borate) containing 3.5 mM aminotheophylline (8-(3-aminopropyl)theophylline) (0.42 μmoles). The reaction yielded a clear solution. Thin layer chromatography confirmed that the aminotheophylline was completely used up. The absorption spectrum of the reaction mixture was similar to that of pure I. In subsequent experiments, the reaction mixture was used without further purification.

The SPR response of the conjugate I-aminotheophylline as compared to pure aminotheophylline was evaluated on the same BIAcore™ instrument as in Example 1. The sensing surfaces were Sensor Chip CM5, as used in Example 1, onto which monoclonal antibodies had been immobilised using the BIAcore™ Amine Coupling Kit (Pharmacia Biosensor AB, Uppsala, Sweden).

Firstly, 35 μM of the conjugate I-aminotheophylline was injected onto three Sensor Chips with somewhat differing amounts of immobilised anti-theophylline antibody. The response varied from 1140 RU (Resonance Units) for the Sensor Chip with the smallest amount of antibody to 1750 RU for the Sensor Chip with the largest amount of antibody. The conjugate dissociated slowly from the antibody when the pulse containing the sample had passed the sensing surface.

Secondly, 35 μM of the conjugate I-aminotheophylline was injected onto an unmodified Sensor Chip and onto a Sensor Chip with immobilised anti-IgE-antibody. The response was on the order of a few hundred RU. In both cases, the response immediately returned to zero when the sample pulse had passed the surface, showing that the response was solely due to the increase in bulk refractive index, and that no adsorption to the surface took place.

Thirdly, 35 μM of pure aminotheophylline was injected onto a Sensor Chip with immobilised anti-theophylline antibody. (The amount of antibody was equal to that of the experiment above that yielded 1140 RU when the conjugate was injected.) The response was 68 RU, and the aminotheophylline dissociated slowly from the antibody when the sample pulse had passed the surface. The enhancement factor when using the conjugate I-aminotheophylline as compared to pure aminotheophylline thus was 1140/68 =17× (neglecting bulk refractive index changes). The concentration of aminotheophylline was chosen to completely saturate the binding sites of the antibody, to assure that the increased response was not due to differences in bound amounts.

Fourthly, a mixture of 1600 μM of aminotheophylline and 32 μM of I-aminotheophylline conjugate was injected onto a Sensor Chip with immobilised anti-theophylline antibody (slightly more antibody than in the previous case). The response during the sample pulse was 340 RU. When the sample pulse had passed the surface, the response slowly decreased due to dissociation of the immune complexes. The response during the dissociation was nevertheless significantly higher than during the dissociation of pure aminotheophylline. This experiment shows that aminotheophylline and the conjugate I-aminotheophylline compete for the same specific sites on the antibody, and that the increased response of the conjugate I-aminotheophylline is not caused by non-specific binding.

EXAMPLE 3

Evaluation of the Enhancement by Labeling of Secondary Antibody in an Assay for Beta-2-Microqlobulin Using a Sandwich Procedure (i) Labeling The so called secondary antibody used in the sandwich assay described below, a polyclonal rabbit antibody against beta-2-microglobulin, was labeled with the dye substance I in Example 2. The substance I (17.1 mg) was reacted with TSU (8.4 mg) in dry dimethylformamide (2.5 ml) for 35 minutes. Dry diethyl ether (10 ml) was added and the precipitate was washed with additional 3×3 ml diethyl ether and dried in a desiccator. 0.6 mg of this material was then reacted with 200 μl of a solution of the polyclonal rabbit antibody against beta-2-microglobulin (2 mg/ml in 0.1 M sodium borate buffer, pH 8.5) for 2 hours at room temperature. The reaction solution was diluted with 600 μl of a phosphate buffer (0.1 M sodium phosphate with 0.1 M sodium chloride, pH 7.0) and eluted on a NAP-10 column (Pharmacia LKB Biotechnology AB, Uppsala, Sweden) in order to remove unreacted dye. The modification degree was evaluated by measuring the absorptions at 280 nm and 750 nm corresponding to antibody and dye, respectively. A modification of approximately 6 dye molecules per antibody was obtained.

(ii) Evaluation in Sandwich Assay

An antibody against beta-2-microglobulin was immobilized to Sensor Chip CM5 in the previously used BIAcore™ instrument by amine coupling using the BIAcore™ Amine Coupling Kit according to manufacturer's recommendations. In sequence, a sample pulse of beta-2-microglobulin (125 ng/ml, 1 min) and a pulse of secondary antibody against beta-2-microglobulin (7 min) were passed over the sensor chip surface. The response was recorded and compared for labeled and unlabeled secondary antibody. An enhancement factor of 2.2 was obtained with the labeled antibody. A control experiment was done in order to measure the amount of non-specific binding by injecting the secondary antibody solutions over a sensor chip surface without previous beta-2-microglobulin pulse. The labeled as well as the unlabeled antibody showed negligible binding to the surface.

I claim:

1. A method of determining the specific binding of a refractive index-enhancing species to a substance on or release of a refractive index-enhancing species from a sensing surface, respectively, comprising:

measuring a change in refractive index at the sensing surface caused by said specific binding of the refractive index-enhancing species to a substance on or release of the refractive index-enhancing species from said sensing surface, wherein the binding or release of said refractive index-enhancing species causes a change in refractive index that varies with wavelength and said measurement is performed using light having a wavelength at or near the maximum of the negative derivative of the absorptivity with respect to wavelength of said refractive index-enhancing species.

2. The method of claim 1, wherein when said wavelength is on the high wavelength side of said maximum, the distance between said wavelength and said maximum is less than 100 nm, and when said wavelength is on the low wavelength side of said maximum, said wavelength is close to said maximum.

3. The method of claim 1 or 2, wherein said assaying is an immunoassay.

4. The method of claim 2, wherein said distance between said wavelength and said maximum is less than 50 nm.

5. The method of claim 1, wherein said refractive index enhancing species comprises a protein or polypeptide conjugated to a chromophore or dye.

6. The method of claim 1, wherein said refractive index enhancing species comprises a hapten conjugated to a chromophore or dye.

7. The method of claim 1, wherein said determining is based upon internal reflection.

8. The method of claim 7, wherein said solid optical surface has a thin metal film thereon, and wherein said determining is based upon surface plasmon resonance.

9. The method of claim 8, wherein said thin metal film is a film of silver or gold.

10. The method of claim 1, wherein said determining is based upon external reflection.

11. The method of claim 1, wherein said assaying is a member selected from the group consisting of a competition assay, a displacement assay, and sandwich assay.

12. A method of assaying for an analyte in a fluid sample, comprising:

providing a sensing surface having immobilized thereto a ligand to which said analyte specifically binds;

determining the refractive index at said sensing surface by using light having a wavelength at or near the maximum of the negative derivative of the absorptivity with respect to wavelength of a refractive index-enhancing species;

contacting said sensing surface with a fluid sample containing or suspected of containing said analyte, as well as with an analyte competitor comprising said analyte or an analyte analogue of said analyte bound to said refractive index-enhancing species; and again determining the refractive index at said sensing surface by using light having a wavelength at or near the maximum of the negative derivative of the absorptivity with respect to wavelength of said refractive index-enhancing species, wherein a change in refractive index at said sensing surface is caused by the specific binding of said analyte bound to said refractive index-enhancing species at said sensing surface.

13. A method of assaying for an analyte in a fluid sample, comprising:

providing a sensing surface having bound thereto a refractive index-enhancing species that can be displaced by said analyte;

determining the refractive index at said sensing surface by using light having a wavelength at or near the maximum of the negative derivative of the absorptivity with respect to wavelength of said refractive index-enhancing species;

contacting said sensing surface with a fluid sample containing or suspected of containing said analyte; and again determining the refractive index at said sensing surface by using light having a wavelength at or near the maximum of the negative derivative of the absorptivity with respect to wavelength of said refractive index-enhancing species, wherein a change in refractive index at said sensing surface is caused by the displacement of said refractive index-enhancing species at said sensing surface by said analyte.

14. A method of assaying for an analyte in a fluid sample, comprising:

providing a sensing surface having immobilized thereto an a ligand to which said analyte specifically binds;

determining the refractive index at said sensing surface by using light having a wavelength at or near the maximum of the negative derivative of the absorptivity with respect to wavelength of a refractive index-enhancing species;

contacting said sensing surface with a fluid sample containing or suspected of containing said analyte;

contacting said sensing surface with said refractive index-enhancing species; and again determining the refractive index at said sensing surface by using light having a wavelength at or near the maximum of the negative derivative of the absorptivity with respect to wavelength of said refractive index-enhancing species;

wherein a change in refractive index at said sensing surface is caused by the specific binding of said refractive index-enhancing-enhancing species at said sensing surface, wherein said refractive index-enhancing species binds to said analyte either before or after said analyte specifically binds to said sensing surface.

* * * * *